(12) United States Patent
Abrahamson et al.

(10) Patent No.: US 7,276,700 B2
(45) Date of Patent: Oct. 2, 2007

(54) METHOD OF ANALYSING A PHARMACEUTICAL SAMPLE

(75) Inventors: Christoffer Abrahamson, Arlöv (SE); Stefan Andersson-Engels, Höör (SE); Staffan Folestad, Mölndal (SE); Jonas Johansson, Mölndal (SE); Mikael Sjöholm, Lund (SE); Gabriel Somesfalean, Lund (SE); Sune Svanberg, Lund (SE)

(73) Assignee: AstraZeneca AB, Sodertalje (SE)

( * ) Notice: Subject to any disclaimer, the term of this patent is extended or adjusted under 35 U.S.C. 154(b) by 189 days.

(21) Appl. No.: 10/507,356

(22) PCT Filed: Mar. 12, 2003

(86) PCT No.: PCT/GB03/01052

§ 371 (c)(1),
(2), (4) Date: May 2, 2005

(87) PCT Pub. No.: WO03/078983

PCT Pub. Date: Sep. 25, 2003

(65) Prior Publication Data

US 2005/0173637 A1   Aug. 11, 2005

(30) Foreign Application Priority Data

Mar. 14, 2002   (SE)  .................................... 0200782

(51) Int. Cl.
  *G01J 5/02*     (2006.01)
  *G01N 21/17*    (2006.01)
(52) U.S. Cl. .............................. 250/339.12; 250/341.8; 250/358.1
(58) Field of Classification Search ........... 250/339.12, 250/341.8
See application file for complete search history.

(56) References Cited

U.S. PATENT DOCUMENTS

| | | | |
|---|---|---|---|
| 4,800,279 A * | 1/1989 | Hieftje et al. .......... | 250/339.09 |
| 5,679,954 A * | 10/1997 | Soloman ................ | 250/339.08 |
| 5,763,884 A | 6/1998 | Hammond et al. | |
| 6,667,802 B2 * | 12/2003 | Faus et al. ................ | 356/300 |
| 6,794,670 B1 * | 9/2004 | Folestad et al. ........... | 250/573 |
| 2002/0125434 A1 * | 9/2002 | Folestad et al. ......... | 250/341.1 |
| 2003/0111607 A1 * | 6/2003 | Bachur et al. ............. | 250/343 |

FOREIGN PATENT DOCUMENTS

| EP | 0 110 502 B1 | 6/1984 |
| EP | 0 458 601 B1 | 11/1991 |
| EP | 0 767 369 A2 | 4/1997 |
| EP | 0 959 342 A2 | 11/1999 |
| WO | WO 00/03229 | 1/2000 |
| WO | WO 01/22063 A1 | 3/2001 |

OTHER PUBLICATIONS

M. Sjöholm, et al., "Analysis of gas dispersed in scattering media"; vol. 26, No. 1 Jan. 1, 2001, Optics Letters, Optical Society of America.

* cited by examiner

*Primary Examiner*—David Porta
*Assistant Examiner*—Frederick F Rosenberger
(74) *Attorney, Agent, or Firm*—White & Case LLP

(57) ABSTRACT

The present invention relates to a method for analysing the amount of free gas within a pharmaceutical sample. According to the invention the method comprises the following steps: providing a sample before an irradiating source; irradiating the sample with at least one beam of electromagnetic radiation; detecting radiation emitted through the sample and generating signals corresponding to the amount of free gas in the sample, and correlating the generated signals to at least one solid state parameter of the sample.

31 Claims, 4 Drawing Sheets

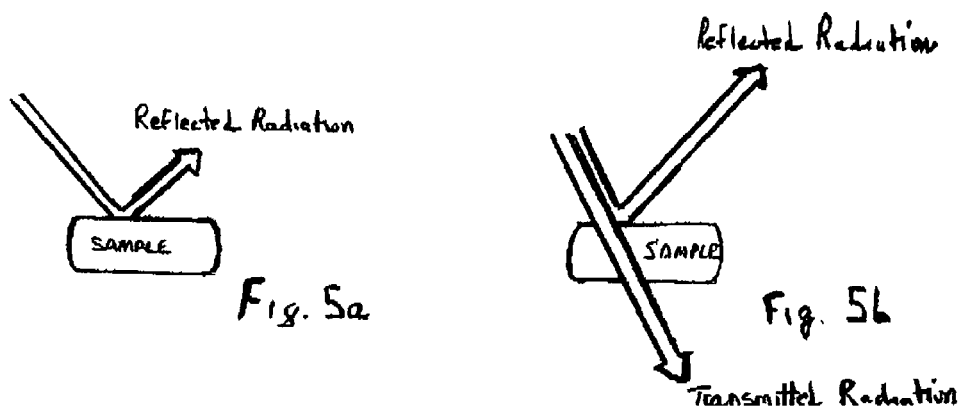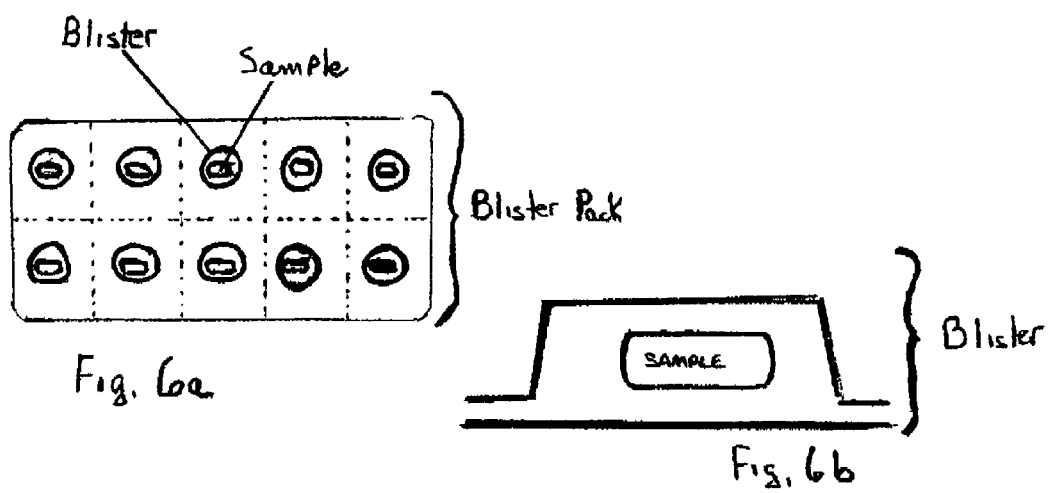

METHOD OF ANALYSING A PHARMACEUTICAL SAMPLE

FIELD OF THE INVENTION

The present invention relates to a method for analysing a pharmaceutical sample, e.g. a tablet, a granule, an encapsulated pellet, a powder, a capsule, a multiple unit pellet system (MUPS) or a similar sample forming a pharmaceutical dose or a sub-fraction of a dose.

BACKGROUND OF THE INVENTION

Optical measurements are becoming increasingly important for analysis within the pharmaceutical industry. Spectroscopy offers the obvious advantages of fast, non-destructive, non-invasive and flexible methods well applicable for analysis near or in the production line. In this context, near-infrared (NIR) spectroscopy is a well-established technique for qualitative and quantitative analysis of the active component and excipients in many different products. In parallel, spectroscopic techniques for measuring structural parameters of pharmaceuticals have been developed; in particular light scattering methods are well known techniques for determination of particle size distribution of powders and solutions. However, determination of physico mechanical parameters of a solid or semi-solid sample is more complex than analysis of chemical content. In fact, for most such physical parameters there is a lack of relevant measurement techniques. For instance, a dissolution testing of a tablet may show that the active component is released too slowly. However, dissolution testing is a technique that measures indirect effects of a deviating sample batch rather than probing the physico-mechanical parameters that are the primary cause of the deviation.

The article "Analysis of gas dispersed in scattering media" from M. Sjöholm et al, Optics Letter, Vol. 26, No. 1 describes how free gas dispersed in scattering materials can be detected and characterised by use of diode laser spectroscopy. Gas detection is made possible by the contrast of the narrow absorptive feature of free-gas molecules as opposed to the small wavelength dependence of the absorption and scattering cross sections in solids and liquids. This method is, however, capable of providing information only regarding the amount of gas, i.e. free oxygen contained in the scattering medium.

SUMMARY OF THE INVENTION

It is an aim of the present invention to provide a method for analysing a pharmaceutical sample, which is capable of providing information as to at least one solid state parameter of the sample.

According to a first aspect of the invention there is provided a method for analysing the amount of free gas within a pharmaceutical sample. According to the invention the method comprises the following steps:
  providing a sample before an irradiating source,
  irradiating the sample with at least one beam of electromagnetic radiation,
  detecting radiation emitted from the sample and generating signals corresponding to the amount of free gas in the sample, and,
  correlating the generated signals to at least one solid state parameter of the sample.

By measuring the content of free gas in solid samples, a correlation to solid state parameters can be achieved. Since the amount of free gas in a sample correlates with the intra particle as well as the interparticle void volume of the sample, an indirect quantitative estimation of specific solid state parameters can be attained.

A solid state parameter relates to both chemical and physical properties of the sample. A pharmaceutical sample consists of a raw material or of a compressed or uncompressed blend of pharmaceutical raw materials. By analysing the sample, information about its chemical as well as its physical parameters may be attained. The meaning of chemical parameters is concentrations of the different components and their distribution within the sample, such as the content of the active substance in a tablet. By physical parameters, on the other hand, is meant the structure, the distribution, the size, the form, the density, the morphology of a sample, particles within the sample, or cavities within the sample. It can also be parameters related to dynamic properties such as heat conduction or gas diffusion within the sample. Thus, the solid state parameters can be divided into static and dynamic solid state parameters.

For example, the solid state parameter may represent the diffusitivity of a gas in a sample, the hardness of a sample, the disintegration ability of a sample, the dissolution ability of a sample, the compressibility of a sample, the aggregation properties of the sample or the flowability of a sample.

One way of performing this measurement is to use an absorption technique, such as wavelength modulation spectroscopy. The wavelength of a light source, preferably a diode laser, is scanned in time such that the wavelength is shifted back and forth across a narrow wavelength region, which includes the absorption wavelength of the free gas to be detected. If the scattering medium contains free gas molecules, these will absorb the radiation in a very narrow wavelength region, giving rise to a tiny, but sharp absorption feature in the intensity of the recorded diffusely scattered light. According to the present invention the free gas is preferably oxygen, carbon dioxide or water vapour.

In order to increase the detection sensitivity a modulation current of high frequency is superimposed on the drive current to the diode laser and the detector signal is picked up phase-sensitively by a lock-in amplifier. The resulting wavelength modulation signal is typically several orders of magnitude larger than that of direct absorption. If the detection is performed at the same frequency or at some harmonic a very sensitive detection is reached. This arrangement can be performed in transmission mode or in reflection mode depending on how the detector is oriented in relation to the light delivery system. Thus, the radiation emitted from the sample may comprise transmitted radiation as well as reflected radiation.

In a first embodiment, the radiation irradiating the sample comprises infrared radiation. Preferably, the infrared radiation is in the near infrared (NIR) spectral region.

More preferably, the radiation has a frequency in the range corresponding to wavelengths of from about 700 to about 2100 nm, particularly from 700 to 1300 nm.

In another embodiment the radiation irradiating the sample comprises visible light.

In still another embodiment the radiation irradiating the sample comprises UV radiation.

The sample to be analysed is a pharmaceutical sample, preferably a solid sample and in particular a tablet, a granule, an encapsulated pellet, a capsule, a bulk powder or an equivalent pharmaceutical dose or fraction of a dose.

Using optical methods for the measurement of free gas in a sample, i.e. air gives several advantages over traditional methods. First, for solid turbid media the light scatters around inside samples in such a way that the entire sample volume is measured. Secondly, optical methods can be used for both large air cavities and for extremely small air micro cavities. Thirdly, using spectroscopic methods fast measurements directly in the production line is possible, either at-line, on-line or in-line. This can be used to generate data for feedback to control the process to obtain precise predetermined product characteristics. Further, this can also be performed at multiple stages within the production line so that not only the end product, such as tablets, is characterised but also raw materials, powders, pellets or granules can be characterised. The latter characterisation can provide an indicator for the success of the following production steps such as tabletting.

The technique of measuring sample gas concentrations with optical spectroscopy and relating that to physical properties of the sample can be used in several manufacturing steps of pharmaceuticals. By measuring the amount of dispersed gas in tablets an indirect correlation to tablet hardness can be reached. This is based on the assumption that the more micro cavities within the sample the higher is the probability of a crack to develop in the tablet.

Measurements of certain solid state parameters, for example tablet hardness are a requirement in manufacturing of pharmaceutical tablets. The tablet hardness in turn affects tablets disintegration properties and release of the active substance in vivo. Hardness measurements are conventionally performed by applying a mechanical force across the tablet by means of two metal legs. As the mechanical force is gradually increased, the tablet breaks at a certain force, which provides a reading of the tablet hardness. This analysis suffers from poor accuracy and precision due to inherent in-homogeneities and microscopic cracks within tablets. In addition, conventional methods for assessing hardness applies the mechanical force in different ways, for example using constant speed or constant force. Thereby different results are obtained for the sample. Furthermore, the analysis requires that tablets are sampled from a production stream and analysed off-line. An optical method, on the other hand, is in general both fast and can be applied within the production line and can also be fairly accurate.

Tablet hardness can according to this invention be related to the amount of encapsulated air within tablets. The harder the tablet matrix is pressed together, the lower amount of air will reside in the tablet. The amount of air within a turbid medium can be determined by measuring the content of molecular oxygen in the sample. Since normal air contains about 21% oxygen, the oxygen measurement may give an indirect quantitative estimation of the tablet hardness.

Measurements performed according to the invention on powders, granules or pellets during or after compression can be used to assess the viscoelastic characteristics of pharmaceutical compacts. For example, by comparing the difference in molecular oxygen in the pharmaceutical compact during compression with that after decompression deformation properties or elasticity of a sample can be monitored.

In another embodiment of the invention the measurement is performed on water vapour rather than on oxygen. By measuring the water vapour content of samples a correlation to the contained moisture within the sample can be attained.

Yet another application is where the invention is used for powder measurements to assess the structure of agglomerates. In this way their bulk properties such as deformation and fracture can be predicted. Because the invention can be applied in situ, for example by conducting measurements in a process vessel, precise control can be obtained in unit operations such as granulation, drying, compaction and transport.

Another application for the present invention is prediction of disintegration/dissolution testing. Pharmaceutical tablets are tested for their dissolution properties in a liquid medium. The conventional rational include putting the tablets in glass vessels filled with heated dissolution medium under agitation of paddles and sampling aliquots of the solution at pre-determined times. The time of an analysis typically ranges between 15 minutes to 24 hours. There is a correlation between the dissolution properties of a sample and its degree of packing, which in turn can be measured with diode laser spectroscopy using the claimed method.

As spectroscopic techniques are fairly fast, dynamic events can be monitored. One such mechanism is diffusion through solid samples. Some pharmaceutical solids, in particular pellets, are built from sub-layers, each layer having a particular property. As an example, an acid-resistant film may be the outer coating on pellets to prevent the pellets from disintegrate already in the upper part of the stomach. Diode laser spectroscopy offers an alternative method of estimating diffusion across coatings. This can be done by preconditioning samples in a nitrogen atmosphere and recording the subsequent diffusion of oxygen into the sample after placing them in normal atmosphere again. The amount of free gas within the sample as a function of time measured by diode laser spectroscopy is correlated with the dynamics of oxygen diffusion. Alternatively the experiment is performed in reversed order starting from a normal atmosphere and following the diffusive exchange of oxygen with nitrogen within the sample.

Physico-mechanical properties of powders may also be assessed by dynamic measurements. A signature of the powders dynamics regarding flowability and packing can be obtained from monitoring a series of consecutive measurements where the sample particles are rearranged continuously by tumbling, mixing or any other particle motion.

DESCRIPTION OF THE DRAWINGS

FIG. 5a illustrates emitted radiation comprising reflected radiation from the sample. FIG. 5b illustrates emitted radiation comprising transmitted radiation and reflected radiation from the sample.

FIG. 6a illustrates a blister pack having 10 blisters containing a pharmaceutical sample. FIG. 6b, is a cross-sectional view of one of the blisters and illustrates a pharmaceutical sample positioned inside the blister.

DESCRIPTION OF THE PREFERRED EMBODIMENTS

One way of performing the measurement according to the present invention is to use an absorption technique, such as wavelength modulation spectroscopy. With this technique the wavelength of a light source, in this case a diode laser is scanned in time such that the wavelength is shifted back and forth across a small wavelength region, which includes the absorption wavelength of a free gas, i.e. oxygen. The diode laser is furthermore modulated at a high frequency and a very sensitive detection at the same frequency or at some harmonic, referred to as lock-in detection, is reached. This arrangement can be performed in a transmission mode or in reflection mode depending on how the detector is oriented in relation to the light delivery system.

Figure 1:
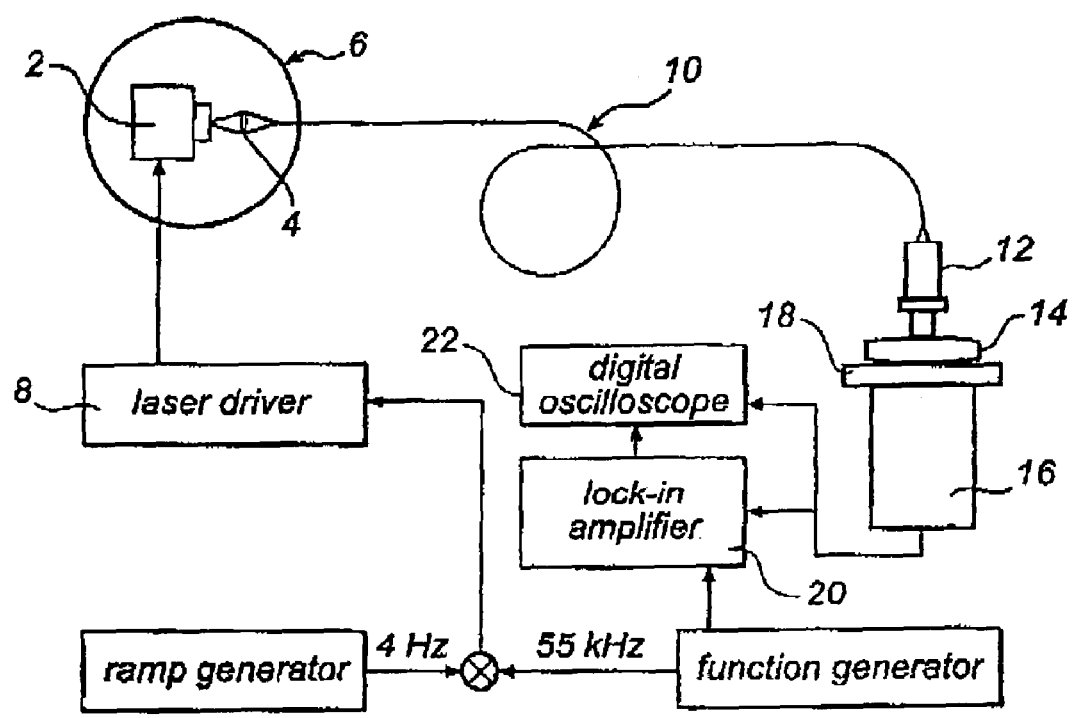
FIG. 1 illustrates the equipment to carry out the method according to the invention.

The measurements of free gas content can be realised in different ways. The use of wavelength modulation diode laser spectroscopy is convenient because of the small size and low cost of these lasers. Together with lock-in technique it constitutes a compact and robust system. Both reflectance and transmission geometries can be employed. The experimental set-up used to prove the concept of tablet hardness measurements with transmission-mode wavelength modulation spectroscopy is shown in FIG. 1. A tunable diode laser 2 with a nominal wavelength of 757 nm together with a focusing lens 4 was positioned inside a chamber 6. The chamber was flushed with nitrogen gas to avoid extra oxygen within the optical path. The diode laser was 2 controlled by a laser driver 8 and the wavelength was tuned by applying a current ramp at 4 Hz. The drive current for the diode laser was mixed with a 55 kHz sinusoidal current component for lock-in amplification. The output light of the diode laser was guided through an optical fibre 10 and collimated by a collimator 12 before being directed to the sample 14. Also the air gap between the distal end of the fibre 10 and the collimator lens was flushed with nitrogen gas. As an alterative, the sample holder (not shown) can be designed to minimise the optical path length through open air, making the nitrogen flow unnecessary. The light transmitted through the sample 14 was collected by a detector 16, in this case a photo multiplier with an optical cut-off filter 18 in front to remove light that did not originate from the laser and was not transmitted through the sample. The signal from the photo multiplier was fed to a lock-in amplifier 20 for phase-sensitive detection of the transmitted light. The extracted second-harmonic component and the direct signal from the photo multiplier 16 were accumulated in a digital oscilloscope 22.

The sample 14 was placed in a sample holder (not shown) between the collimator 12 and the detector 16 for measurements to mask off any stray light not going through the sample. Several samples were measured and after that the tablet hardness was measured with a conventional instrument. A blank spectrum of an empty sample holder was measured for comparison. For the first sample the signal was measured for several collimator-detector distances and the standard-addition approach was utilised to achieve absolute measures of the amount of oxygen within the detection path.

Figure 2A:
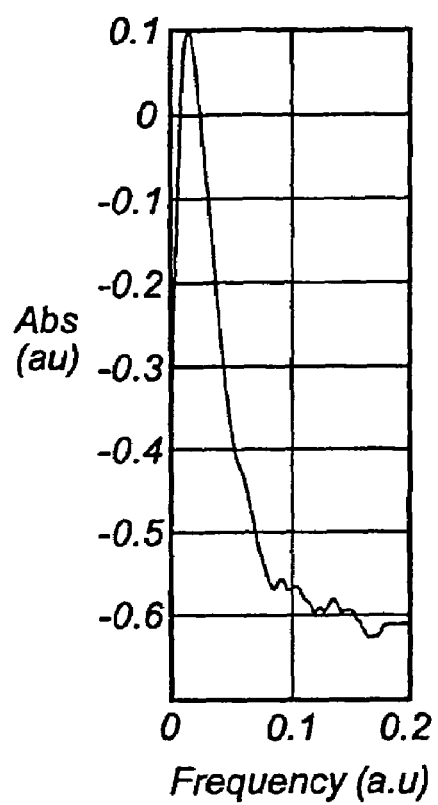
FIGS. 2a-c show three raw spectra illustrating the oxygen concentration in a sample wherein the light absorption is shown as a function of frequency for a) a blank sample; b) a sample from a first batch, and c) a sample from a second batch.
Figure 2B:
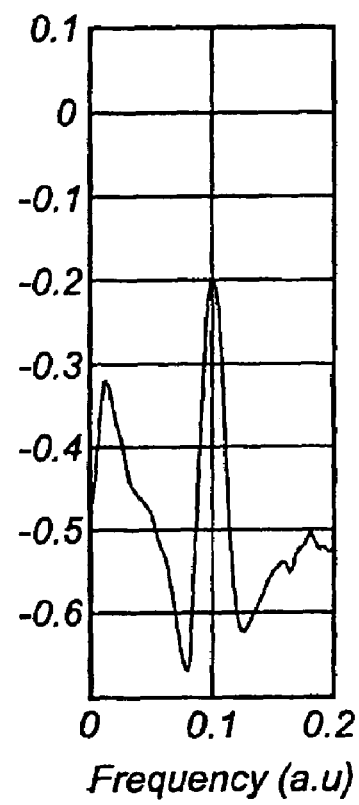
Figure 2C:
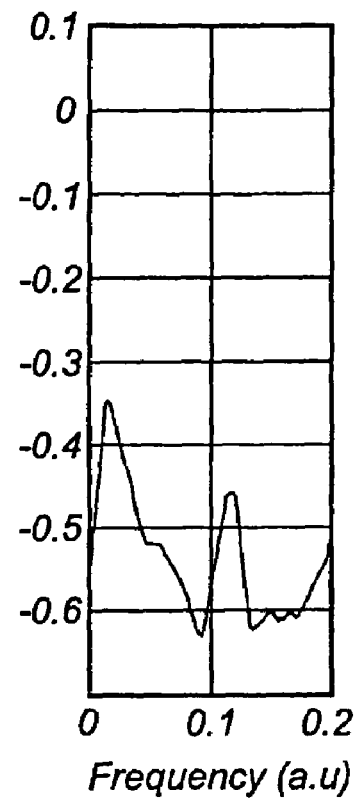

FIGS. 2a-2c show raw spectra of the oxygen concentration in a sample as a function of frequency. FIG. 2a is an example of wavelength modulation signals of a blank (no sample), and FIGS. 2b and 2c show signals from two different samples, i.e: tablets from batch A and batch B respectively. The oxygen peak for each sample can be seen at approximately the frequency 0.1 in arbitrary units (a.u.).

Figure 3:
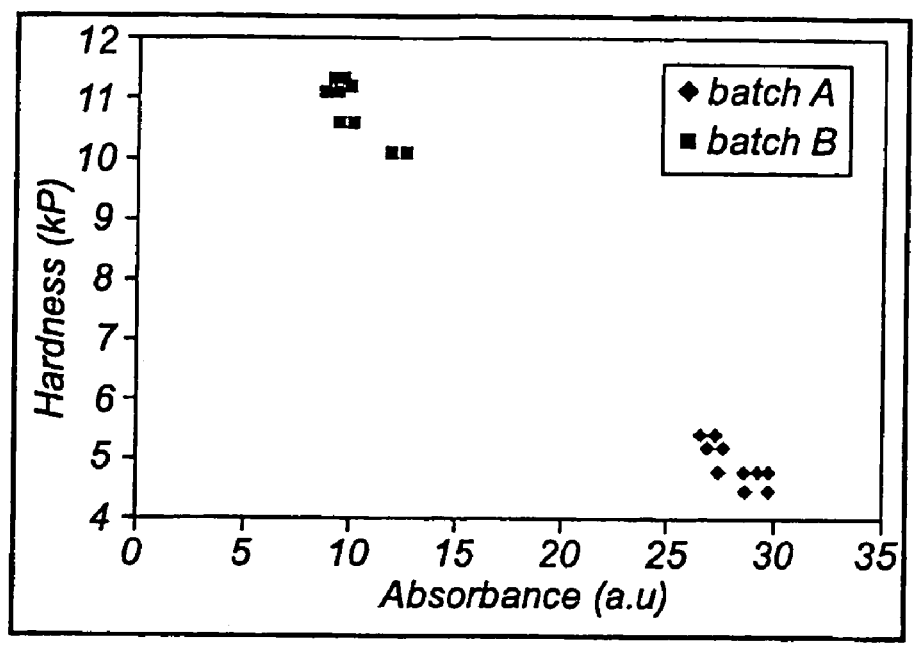
FIG. 3 illustrates the hardness of a number of samples from two different batches, batch A and batch B, as a function of light absorption.

In FIG. 3, a correlation plot for a number of tablets from the two different batches, batch A and batch B, shows the tablet hardness (kP) measured with a conventional method as a function of the absorption signal (a.u.) measured with the new method. As can be seen there is a correlation between the conventional and the novel measuring technique.

Figure 4:
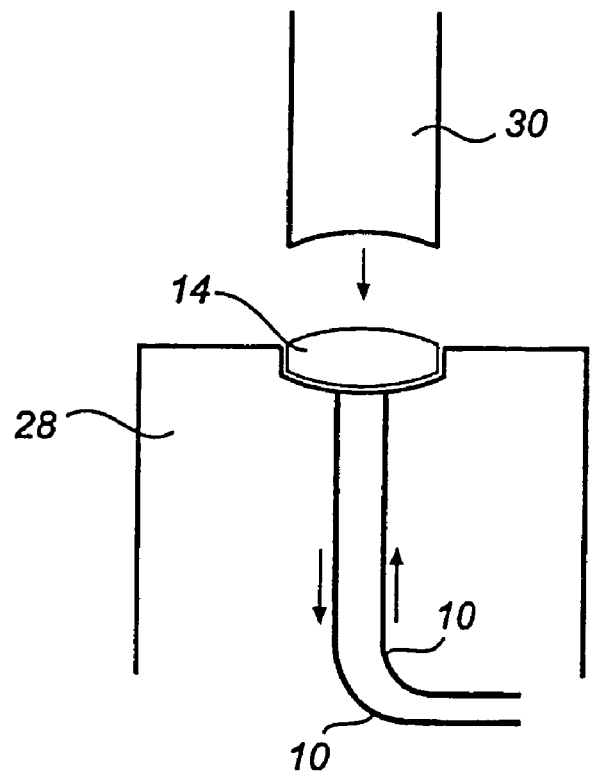
FIG. 4 illustrates the equipment to carry out measurements according to the invention during compaction of powders, i.e. a tabletting process.

In FIG. 4 is shown an example where the invention and measurement system described in FIG. 1 is applied to monitor changes in a bulk powder sample 14 during compaction. The light guides 10 are here arranged to illuminate the sample within the compaction equipment comprising a die 28 and a punch 30. This measurement can be performed in situ in a tabletting machine, thereby enabling in-line measurements in the manufacturing process. This can also be performed in a test system at-line from the process. In both cases, generated data can be used to predict physicomechanical properties of the samples that can be used as feedback control data in the process to obtain predetermined product characteristics.

The invention claimed is:

1. A method for controlling the manufacture of a pharmaceutical sample, the method comprising the steps of:
   a) providing the pharmaceutical sample before an irradiating source;
   b) irradiating the pharmaceutical sample with at least one beam of electromagnetic radiation;
   c) detecting radiation emitted from the pharmaceutical sample;
   d) generating signals corresponding to the amount of free gas in the pharmaceutical sample; and,
   e) controlling the method by using the detected amount of free gas in the pharmaceutical sample as feedback control data and correlating the generated signals to at least one solid state parameter of the pharmaceutical sample.

2. The method according to claim 1, wherein the emitted radiation comprises transmitted radiation from the pharmaceutical sample.

3. The method according to claim 1, wherein the emitted radiation comprises reflected radiation from the pharmaceutical sample.

4. The method according to claim 1, wherein the emitted radiation comprises transmitted radiation and reflected radiation from the pharmaceutical sample.

5. The method according to claim 1, wherein the free gas is oxygen.

6. The method according to claim 1, wherein the free gas is carbon dioxide.

7. The method according to claim 1, wherein the free gas is water vapour.

8. The method according to claim 1, further comprising the step of detecting radiation emitted as a function of time.

9. The method according to claim 1, wherein the solid state parameter represents the hardness of the sample.

10. The method according to claim 1, wherein the solid state parameter represents the disintegrability of the pharmaceutical sample.

11. The method according to claim 1, wherein the solid state parameter represents the dissolvability of the pharmaceutical sample.

12. The method according to claim 1, wherein the solid state parameter represents the flowability of the pharmaceutical sample.

13. The method according to claim 1, wherein the solid state parameter represents the aggregation properties of the pharmaceutical sample.

14. The method according to claim 1, wherein the solid state parameter represents the density of the pharmaceutical sample.

15. The method according to claim 1, wherein the pharmaceutical sample is a solid sample.

16. The method according to claim 15, wherein the pharmaceutical sample is positioned inside a blister of a blister pack.

17. The method according to claim 15, wherein the solid sample is selected from the group consisting of a tablet, a granule, a capsule, a bulk powder, a pharmaceutical dose, and a pharmaceutical dosage form.

18. The method according to claim 1, wherein the radiation irradiating the sample comprises infrared (IR) radiation.

19. The method according to claim 18, wherein the IR radiation is near infrared (NIR) radiation.

20. The method according to claim 1, wherein the radiation has a wavelength in the range of from about 700 to about 2100 nm.

21. The method according to claim 20, wherein the radiation has a wavelength in the range of from about 700 to about 1300 nm.

22. The method according to claim 1, wherein the radiation irradiating the pharmaceutical sample comprises visible light.

23. The method according to claim 1, wherein the radiation irradiating the pharmaceutical sample comprises UV radiation.

24. The method according to claim 1, wherein the irradiating source comprises a diode laser.

25. The method according to claim 1, wherein the emitted radiation is detected by a photo multiplier.

26. The method according to claim 1, wherein the emitted radiation is detected by a photo diode.

27. The method according to claim 1, wherein the analysis is conducted in a manufacturing area at-line.

28. The method according to claim 1, wherein the analysis is conducted in a manufacturing area on-line.

29. The method according to claim 1, wherein the analysis is conducted in-line in a manufacturing process vessel.

30. The method according to claim 1, wherein the solid state parameter represents the diffusitivity of a gas in the pharmaceutical sample.

31. The method according to claim 1, wherein the generated signals are correlated to more than one solid state parameter of the sample.

* * * * *